US012122922B2

(12) United States Patent
Large et al.

(10) Patent No.: US 12,122,922 B2
(45) Date of Patent: Oct. 22, 2024

(54) PICKERING EMULSIONS

(71) Applicant: THE UNIVERSITY OF SUSSEX, Brighton (GB)

(72) Inventors: Matthew James Large, Brighton (GB); Alan Brian Dalton, Brighton (GB); Sean Paul Ogilvie, Brighton (GB)

(73) Assignee: The University of Sussex, Brighton (GB)

( * ) Notice: Subject to any disclaimer, the term of this patent is extended or adjusted under 35 U.S.C. 154(b) by 1050 days.

(21) Appl. No.: 16/960,705

(22) PCT Filed: Jan. 7, 2019

(86) PCT No.: PCT/GB2019/050033
§ 371 (c)(1),
(2) Date: Jul. 8, 2020

(87) PCT Pub. No.: WO2019/135094
PCT Pub. Date: Jul. 11, 2019

(65) Prior Publication Data
US 2020/0399481 A1   Dec. 24, 2020

(30) Foreign Application Priority Data
Jan. 8, 2018   (GB) ..................... 1800249

(51) Int. Cl.
*C09D 11/023*   (2014.01)
*C01B 32/19*   (2017.01)
(Continued)

(52) U.S. Cl.
CPC ............ *C09D 11/023* (2013.01); *C01B 32/19* (2017.08); *C01B 32/194* (2017.08);
(Continued)

(58) Field of Classification Search
CPC ... C09D 11/023; C09D 11/033; C09D 11/037; C09D 11/101; C09D 11/322;
(Continued)

(56) References Cited

U.S. PATENT DOCUMENTS 4,996,108 A * 2/1991 Divigalpitiya ........ C01B 19/007
427/430.1
2007/0073201 A1 * 3/2007 Campagna ............ A61F 13/041
602/8
(Continued)

FOREIGN PATENT DOCUMENTS

EP   0382339 A1   8/1990
WO   2011087913 A1   7/2011
(Continued)

OTHER PUBLICATIONS

Hassan, Mahbub, et al. "High-Yield Aqueous Phase Exfoliation of Graphene for Facile Nanocomposite Synthesis via Emulsion Polymerization." Journal of Colloid and Interface Science, vol. 410, 2013, pp. 43-51., https://doi.org/10.1016/j.jcis.2013.08.006. (Year: 2013).*
(Continued)

*Primary Examiner* — Jennifer A Smith
*Assistant Examiner* — Jeffrey Eugene Barzach
(74) *Attorney, Agent, or Firm* — Meunier Carlin & Curfman LLC

(57) ABSTRACT

The present invention relates to a method for making a Pickering emulsion, the method comprising: exfoliating a non-silicate layered 3D material in a solvent to produce particles of a non-silicate unfunctionalised 2D material; forming a dispersion of the particles of the 2D material in a first liquid phase; adding a second liquid phase; and homogenising the dispersion of the 2D material in the first liquid phase with the second liquid phase to form a Pickering
(Continued)

emulsion comprising the first liquid phase, the second liquid phase, and the particles of the 2D material.

19 Claims, 10 Drawing Sheets

(51) Int. Cl.
  C01B 32/194 (2017.01)
  C09D 11/033 (2014.01)
  C09D 11/037 (2014.01)
  C09D 11/101 (2014.01)
  C09D 11/322 (2014.01)
  C09D 11/52 (2014.01)

(52) U.S. Cl.
  CPC .......... *C09D 11/033* (2013.01); *C09D 11/037* (2013.01); *C09D 11/101* (2013.01); *C09D 11/322* (2013.01); *C09D 11/52* (2013.01)

(58) Field of Classification Search
  CPC ......... C09D 11/52; C09D 11/36; C01B 32/19; C01B 32/194; C01B 19/007; C01B 21/0648; C01B 2204/22; C01B 2204/28; A61K 2800/10; A61K 8/19; A61K 8/06; A61Q 19/00; C01P 2004/02; C01G 39/06; C01G 41/00; G01B 7/18; G01B 13/24; G01L 1/20
  See application file for complete search history.

(56) References Cited

U.S. PATENT DOCUMENTS

| | | | |
|---|---|---|---|
| 2009/0005529 A1* | 1/2009 | Lai ........................ | C07C 329/00 526/318.6 |
| 2010/0183716 A1* | 7/2010 | Koo ...................... | C07D 213/42 514/357 |
| 2016/0114325 A1* | 4/2016 | Tang ................. | B01L 3/502761 436/180 |
| 2017/0178762 A1 | 6/2017 | Adamson et al. | |
| 2019/0181273 A1* | 6/2019 | van Rooyen ..... | H01L 29/42384 |

FOREIGN PATENT DOCUMENTS

| WO | 2012028724 A1 | 3/2012 |
|---|---|---|
| WO | 2014001519 A1 | 1/2014 |
| WO | 2015082890 A1 | 6/2015 |

OTHER PUBLICATIONS

"PB4 Impeller." Industrial Mixing Equipment by Fusion, Fluid Fusion Equipment, https://fusionfluid.com/products/mixing-impellers/pitch-blade-turbine-4-blade-pb4. (Year: 2023).*
Woltornist, Steven J., et al. "Conductive Thin Films of Pristine Graphene by Solvent Interface Trapping." ACS Nano, vol. 7, No. 8, 2013, pp. 7062-7066., https://doi.org/10.1021/nn402371c. (Year: 2013).*
Yi, Min, et al. "Water Can Stably Disperse Liquid-Exfoliated Graphene." Chemical Communications, vol. 49, No. 94, 2013, p. 11059., https://doi.org/10.1039/c3cc46457a. (Year: 2013).*
Hodge, Stephen A., et al. "Microfluidization of Graphite and Formulation of Graphene-Based Conductive Inks." ACS Nano, vol. 11, No. 3, 2017, pp. 2742-2755., https://doi.org/10.1021/acsnano.6b07735. (Year: 2017).*
Boxall, John A., et al. "Droplet Size Scaling of Water-in-Oil Emulsions under Turbulent Flow." Langmuir, vol. 28, No. 1, 2011, pp. 104-110., https://doi.org/10.1021/la202293t. (Year: 2011).*
Du, Wencheng, et al. "From Graphite to Graphene: Direct Liquid-Phase Exfoliation of Graphite to Produce Single- and Few-Layered Pristine Graphene." Journal of Materials Chemistry A, vol. 1, No. 36, 2013, p. 10592., https://doi.org/10.1039/c3ta12212c. (Year: 2013).*
Gonzalez Ortiz, Danae, et al. "Inverse Pickering Emulsion Stabilized by Exfoliated Hexagonal-Boron Nitride (h-BN)." Langmuir, vol. 33, No. 46, 2017, pp. 13394-13400., https://doi.org/10.1021/acs.langmuir.7b03324. (Year: 2017).*
Quinn, Matthew D., et al. "Photothermal Breaking of Emulsions Stabilized with Graphene." ACS Applied Materials & Interfaces, vol. 8, No. 16, 2016, pp. 10609-10616., https://doi.org/10.1021/acsami.6b00737. (Year: 2016).*
Vignesh, et al. "Study of sonication assisted synthesis of molybdenum disulfide (MOS2) nanosheets." Materials Today: Proceedings, vol. 21, 2020, pp. 1969-1975, https://doi.org/10.1016/j.matpr.2020.01.313. (Year: 2020).*
Guardia, Laura, et al. "Production of aqueous dispersions of inorganic graphene analogues by exfoliation and stabilization with non-ionic surfactants." RSC Adv., vol. 4, No. 27, 2014, pp. 14115-14127, https://doi.org/10.1039/c4ra00212a. (Year: 2014).*
Wang, Zhongying, and Baoxia Mi. "Environmental applications of 2D molybdenum disulfide (MOS2) nanosheets." Environmental Science & Technology, vol. 51, No. 15, 2017, pp. 8229-8244, https://doi.org/10.1021/acs.est.7b01466. (Year: 2017).*
Biswas, Sanjib, and Lawrence T. Drzal. "A novel approach to create a highly ordered monolayer film of graphene nanosheets at the liquid-liquid interface." Nano Letters, vol. 9, No. 1, 2009, pp. 167-172, https://doi.org/10.1021/nl802724f. (Year: 2009).*
Hernandez, Yenny, et al. "Measurement of multicomponent solubility parameters for graphene facilitates solvent discovery." Langmuir, vol. 26, No. 5, 2009, pp. 3208-3213, https://doi.org/10.1021/la903188a. (Year: 2009).*
International Search Report and Written Opinion in PCT/GB2019/050033. Mailed Mar. 4, 2019. 21 pages.
Danae Gonzalez Ortiz et al: "Inverse Pickering Emulsion Stabilized by Exfoliated Hexagonal-Boron Nitride (h-BN)", Langmuir, vol. 33, No. 46, Oct. 31, 2017, pp. 13394-13400, XP055558197.
Matthew D. J. Quinn et al: "Photothermal Breaking of Emulsions Stabilized with Graphene", ACS Applied Materials & Interfaces, vol. 8, No. 16, Apr. 7, 2016, pp. 10609-10616, XP055558349.
C. S. Boland et al: "Sensitive electromechanical sensors using viscoelastic graphene-polymer nanocomposites", Science, vol. 354, No. 6317, Dec. 9, 2016, pp. 1257-1260, XP055558622.
Karagiannidis P G et al: "Microfluidization of graphite and formulation of graphene-based conductive inks", arxiv.org, Cornell University Library, 201 Olin Library Cornell University Ithaca, NY 14853, Nov. 11, 2016, XP080731640.
Lin, Andrew Kun-Yi et al. "Magnetically controllable Pickering emulsion prepared by a reduced graphene oxide-iron oxide composite". Journal of Colloid and Interface Science. 438 (2015) 296-305. Jul. 22, 2014.
Tang, Mingyi et al. "Factors that affect the stability, type and morphology of Pickering emulsion stabilized by silver nanoparticles/graphene oxide nanocomposites". Materials Research Bulletin 60 (2014) 118-129. Mar. 25, 2014.
Luo, Qinmo et al. "Hollow microcapsules by stitching together of graphene oxide nanosheets with a di-functional small molecule". Carbon 105 (2016) 125-131. Feb. 22, 2016.
Wu, Yinglei et al. "The emulsifying and tribiological properties of modified graphene oxide in oil-in-water emulsion". Tribiology International 105 (2017) 301-316. Mar. 29, 2016.
Shen, Jeffrey et al. "Liquid Phase Exfoliation of Two-Dimensional Materials by Directly Probing and Matching Surface Tension Components". Nano Lett. 2015, 15, 5449-5454. May 10, 2015.
Hernandez, Yenny et al. "High-yield production of graphene by liquid-phase exfoliation of graphite". nature nanotechnology | vol. 3 | Sep. 2008 | www.nature.com/naturenanotechnology.
Hernandez, Yenny et al. "Measurement of Multicomponent Solubility Parameters for Graphene Facilitates Solvent Discovery". American Chemical Society pubs.acs.org/Langmuir. Aug. 26, 2009.
Daradmare, Sneha et al. "Encapsulating 8-hydroxyquinoline in graphene oxide-stabilized polystyrene containers and its anticorrosion performance". J Mater Sci (2016) 51:10262-10277. Jun. 1, 2016.

(56) References Cited

OTHER PUBLICATIONS

Tang, Mingyi et al. "Au nanoparticle/graphene oxide hybrids as stabilizers for Pickering emulsions and Au nanoparticle/graphene oxide@polystyrene microspheres". Science Direct, Carbon 71 (2014) 238-248. Oct. 18, 2013.
Woltornist, Steven J., et al. "Conductive thin films of pristine graphene by solvent interface trapping." ACS nano 7.8 (2013): 7062-7066.
Woltornist, Steven J., et al. "Polymer/pristine graphene based composites: From emulsions to strong, electrically conducting foams." Macromolecules 48.3 (2015): 687-693.

\* cited by examiner

Figure 9

| Solvent | Pentane | Hexane | Ethyl acetate | Cyclohexane | Chloroform | Dichloromethane | MMA | Styrene | CPO | CHO | CHP | NMP | Ethylene glycol | Diethylene glycol | Formamide | Glycerol | Water |
|---|---|---|---|---|---|---|---|---|---|---|---|---|---|---|---|---|---|
| Surface tension | 15 | 19 | 23 | 25 | 27 | 28 | 28 | 32 | 33 | 34 | 35 | 41 | 47 | 55 | 57 | 64 | 72 |
| Pentane | | | | | | | | | | | | | | | | | |
| Hexane | 0 | | | | | | | | | | | | | | | | |
| Ethyl acetate | 0 | 0 | | | | | | | | | | | | | | | |
| Cyclohexane | 0 | 0 | 0 | | | | | | | | | | | | | | |
| Chloroform | 0 | 0 | 0 | 0 | | | | | | | | | | | | | |
| Dichloromethane | 0 | 0 | 0 | 0 | 0 | | | | | | | | | | | | |
| MMA | 0 | 0 | 0 | 0 | 0 | 0 | | | | | | | | | | | |
| Styrene | 0 | 0 | 0 | 0 | 0 | 0 | 0 | | | | | | | | | | |
| CPO | 0 | 0 | 0 | 0 | 0 | 0 | 0 | 0 | | | | | | | | | |
| CHO | 0 | 0 | 0 | 0 | 0 | 0 | 0 | 0 | 0 | | | | | | | | |
| CHP | 0 | 0 | 0 | 0 | 0 | 0 | 0 | 0 | 0 | 0 | | | | | | | |
| NMP | 1 | 1 | 0 | 0 | 0 | 0 | 0 | 0 | 0 | 0 | 0 | | | | | | |
| Ethylene glycol | 1 | 1 | 1 | 1 | 1 | 1 | 1 | 1 | 0 | 0 | 0 | 0 | | | | | |
| Diethylene glycol | 1 | 1 | 0 | 1 | 0 | 0 | 1 | 0 | 0 | 0 | 0 | 0 | | | | | |
| Formamide | 1 | 1 | 0 | 1 | 1 | 1 | 1 | 1 | 0 | 0 | 0 | 0 | 0 | | | | |
| Glycerol | 1 | 1 | 1 | 1 | 1 | 1 | 1 | 1 | 1 | 1 | 0 | 0 | 0 | 0 | | | |
| Water | 1 | 1 | 1 | 1 | 1 | 1 | 1 | 1 | 1 | 1 | 0 | 0 | 0 | 0 | 0 | | |

PICKERING EMULSIONS

CROSS REFERENCE TO RELATED APPLICATIONS

This application is a United States National Phase Patent Application of International Patent Application Number PCT/GB2019/050033, filed on Jan. 7, 2019, which claims priority to GB Patent Application No. 1800249.3, filed on Jan. 8, 2018, both of which are incorporated by reference herein in their entireties.

FIELD OF THE INVENTION

The present invention relates to Pickering emulsions comprising a two-dimensional (2D) solid, as well as a method of making said emulsions and uses of the emulsions.

BACKGROUND OF THE INVENTION

Two-dimensional (2D) materials, sometimes called single layer materials, are crystalline materials consisting of a few layers, or even just a single layer (monolayer), of atoms or molecules. A wide range of 2D materials are known, including graphene, hexagonal boron nitride (h-BN), and transition metal dichalcogenides (TMDs). TMDs have the formula $MX_2$, wherein M is a transition metal and X is a chalcogen atom (S, Se or Te). Examples of TMDs include molybdenum disulphide ($MoS_2$), niobium diselenide ($NbSe_2$) and tungsten disulphide ($WS_2$).

2D materials are known to have many interesting and potentially useful properties, which differ from the properties of the corresponding bulk 3D material. For example, graphene is highly conductive and has applications in electrode structures as well as conductive composites. Hexagonal boron nitride is electrically insulating but has a large thermal conductivity, and so has applications in thermal management. 2D molybdenum disulphide is a semiconductor with uses in catalysis applications and has spectral features that are sensitive to the dielectric environment of the particulates, a feature which is useful in sensing applications.

The interesting functional properties of many materials are often only observed when the materials are in their mono- or few-layer (i.e. 2D) forms. However, strong inter-layer dispersion forces must be overcome in order to exfoliate bulk three-dimensional (3D) materials to form the corresponding 2D materials.

Various methods of forming 2D materials are known, including the intercalation of species such as ions between the layers of a 3D material, thereby weakening the interlayer adhesion. Other known methods include subjecting a layered 3D material such as graphite to ultrasound in a suitable solvent. Such methods are known from, for example, WO 2012/028724 and WO 2014/001519. Alternatively, a 3D layered material may be subjected to shear forces when in a liquid to produce a 2D material, as described in US 2016/0009561.

However, even after 2D materials are formed, strong inter-layer dispersion forces drive re-aggregation of the 2D materials. For example, if the 2D material is formed by ultrasonication, the 2D material must then be stabilised against re-aggregation. Re-aggregation has been a long-standing roadblock to utilisation of 2D materials in macroscopic material systems at industrially relevant scales. The Applicant has found that a Pickering emulsion can be used to stabilise 2D materials.

Pickering emulsions are emulsions that are stabilized by solid particles which adsorb at the interface between two liquid phases in the emulsion. Such solid-stabilized emulsions are known to be extremely stable, and unlike many surfactant-stabilised emulsions are not susceptible to spontaneous phase separation.

Pickering emulsions have previously been stabilised using solids such as silica and surface-modified or functionalised clays (silicates). However, these solids have been used simply to stabilise a Pickering emulsion, and do not impart functionality to the emulsion.

US 2015/0348669 discloses a method for the production of a composite formed from an emulsion comprising graphite/graphene. US 2014/0305571 discloses a method for the production of films and coatings using emulsions comprising graphite/graphene. However, the methods disclosed in these applications simply comprise sonicating a mixture of liquids and graphite. There is therefore no control over the formation of the graphene/graphite layers in the emulsion, and there is no guarantee that the graphite will be successfully exfoliated to form monolayers of graphene.

It would be desirable to form Pickering emulsions using non-silicate 2D materials that are formed in a controlled manner, in order to ensure a controlled process for providing both stability and functionality to the emulsion.

SUMMARY OF THE INVENTION

In one aspect, the present invention provides a method of making a Pickering emulsion comprising:
  (a) exfoliating a non-silicate layered 3D material in a solvent to produce particles of a non-silicate unfunctionalised 2D material;
  (b) forming a dispersion of the particles of the 2D material in a first liquid phase; and
  (c) adding a second liquid phase and homogenising the dispersion of the 2D material in the first liquid phase with the second liquid phase to form a Pickering emulsion comprising the first liquid phase, the second liquid phase, and the particles of the 2D material.

One of the first and second liquid phases forms a continuous phase in the emulsion, whilst the other forms a dispersed (or discontinuous) phase (i.e. droplets) in the emulsion. The particles of the 2D material adsorb at the interface between the continuous and dispersed phases, thus stabilising the emulsion.

In order to form a Pickering emulsion, one of the liquid phases should have a surface tension which is higher than the surface tension of the 2D material, and the other liquid phase should have a surface tension which is lower than the surface tension of the 2D material. In addition, the first and second liquid phases should be immiscible.

In another aspect, the present invention provides a Pickering emulsion produced by the method of the invention.

Pickering emulsions formed using the method of the present invention can be used in the liquid form as, for example, thermal management liquids, fluid conductors or as inks. Alternatively, the emulsions can be dried or polymerised to form solid structures, which may be used, for example, to produce tailored materials for energy storage applications.

In another aspect, the invention provides a liquid strain sensor comprising a Pickering emulsion which is stabilised by a non-silicate unfunctionalised 2D material, such as the Pickering emulsion formed using the method of the present invention, wherein the 2D material is electrically conductive. In such sensors, the Pickering emulsion is preferably contained within a closed pipe or channel.

In another aspect, the invention provides an electrically conductive ink comprising a Pickering emulsion which is stabilised by a non-silicate unfunctionalised 2D material, such as the Pickering emulsion formed using the method of the present invention, preferably wherein the 2D material is electrically conductive.

In another aspect, the present invention provides a Pickering emulsion which is stabilised by a non-silicate unfunctionalised 2D material, such as the Pickering emulsion formed using the method of the present invention, wherein the emulsion comprises a continuous liquid phase and a dispersed liquid phase, and wherein the dispersed liquid phase is in the form of droplets having an average diameter of about 50 μm or less, preferably about 20 μm or less, more preferably about 10 μm or less.

In another aspect, the present invention provides a Pickering emulsion which is stabilised by a non-silicate unfunctionalised 2D material, such as the Pickering emulsion formed using the method of the present invention, wherein the 2D material is not graphene or boron nitride.

In another aspect, the present invention provides a Pickering emulsion stabilised by a non-silicate unfunctionalised 2D material, such as the Pickering emulsion formed using the method of the present invention, wherein the emulsion comprises a continuous liquid phase and a dispersed liquid phase, and wherein the amount of 2D material present in the emulsion is from about 0.0001 to about 1 vol. %, based on the volume of the dispersed phase.

LIST OF FIGURES

FIG. 9 is a table which indicates whether a range of liquid phases are immiscible or miscible with each other.

DETAILED DESCRIPTION OF THE INVENTION

Figure 1:
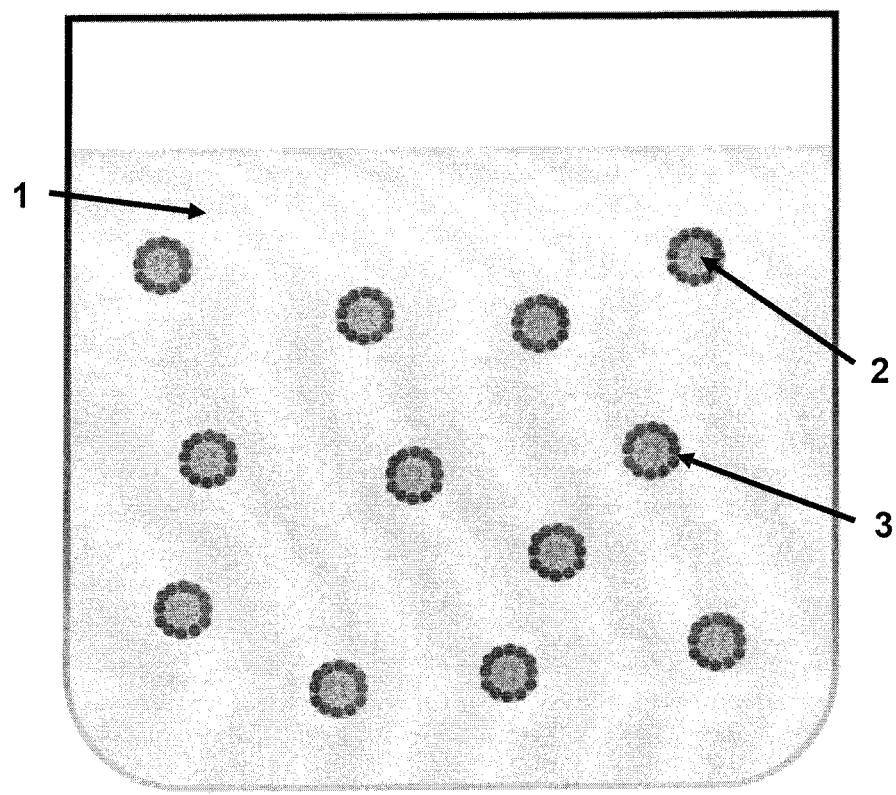
FIG. 1 is a schematic illustration of a traditional surfactant-stabilised emulsion.
Figure 2:
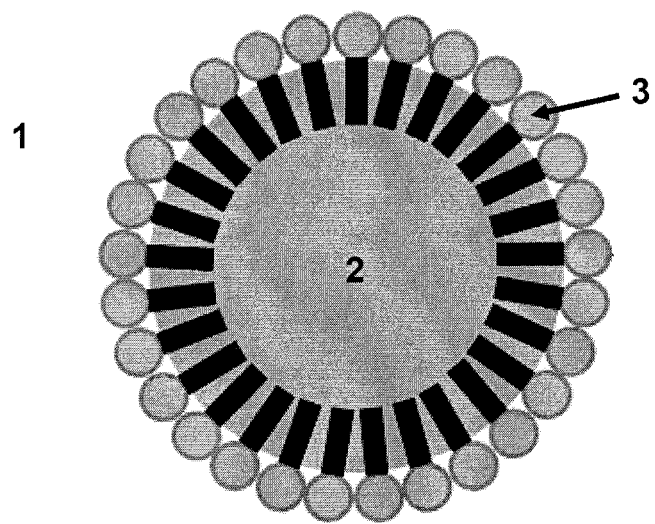
FIG. 2 is a schematic illustration of a surfactant-stabilised droplet within a traditional surfactant-stabilised emulsion.

As is well known in the art, an emulsion is a mixture of two or more immiscible liquids, where droplets of one liquid (the dispersed or discontinuous phase) are dispersed in the other liquid (the continuous phase). Examples of emulsions include vinaigrettes, homogenized milk and mayonnaise. Emulsions often comprise surfactants, which act to stabilise the emulsion by increasing its kinetic stability. Surfactants generally have a polar or hydrophilic part, and a non-polar or hydrophobic part. The surfactant molecules orientate themselves with the polar portion towards the more polar liquid phase, and the non-polar portion towards the less polar liquid phase. They therefore form a layer between the dispersed and continuous phases, which helps stabilise the emulsion. FIG. 1 shows an emulsion comprising a continuous phase (1) and a dispersed phase (2), with surfactant molecules (3) forming a stabilising layer between the two phases. FIG. 2 shows one of the surfactant-stabilised droplets within the emulsion shown in FIG. 1.

Figure 3:
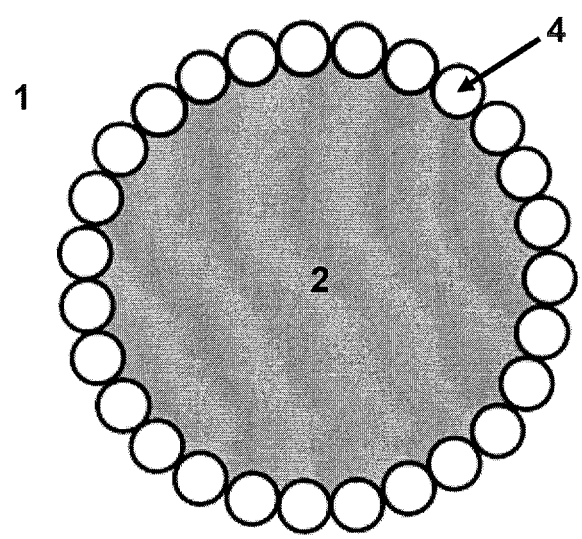
FIG. 3 is a schematic illustration of a droplet within a Pickering emulsion.

A Pickering emulsion is an emulsion that is stabilised by solid particles, which adsorb at the interface between two liquid phases in the emulsion. FIG. 3 shows a solid-stabilised droplet within a Pickering emulsion, comprising a continuous phase (1) and a dispersed phase (2), and solid particles (4) which form a layer between the two phases.

The present invention provides a method for forming a Pickering emulsion which comprises a non-silicate unfunctionalised 2D material as the solid particles which adsorb at the interface between the dispersed liquid phase and the continuous liquid phase.

Non-Silicate Unfunctionalised 2D Material

The 2D material used in the present invention may be any 2D material which is not a silicate and which is unfunctionalised. Graphene oxide and silicates, including silica, clays, functionalised clays, and surface modified clays, are not therefore included in the definition of suitable 2D materials for use in the present invention.

Suitable unfunctionalised 2D materials for use in the present invention include graphene, borophene, germanene, silicene, stanene, phosphorene, bismuthene, hexagonal boron nitride (h-BN), MXenes, 2D perovskites and transition metal dichalcogenides (TMDs). TMDs have the formula $MX_2$, wherein M is a transition metal and X is a chalcogen atom (S, Se or Te). Examples of TMDs include molybdenum disulphide ($MoS_2$), molybdenum diselenide ($MoSe_2$), molybdenum ditelluride ($MoTe_2$), niobium diselenide ($NbSe_2$), tungsten disulphide ($WS_2$), tungsten diselenide ($WSe_2$) and hafnium disulphide ($HfS_2$). MXenes are 2D materials consisting of layers of transition metal carbides, nitrides or carbonitrides which are a few atoms thick. Examples include $Ti_2C$, $V_2C$, $Nb_2C$, $Mo_2C$, $Ti_3C_2$, $Ti_3CN$, $Zr_3C_2$, $Hf_3C_2$, $Ti_4N_3$, $Nb_4C_3$, $Ta_4C_3$, $Mo_2TiC_2$, $Cr_2TiC_2$ and $Mo_2Ti_2C_3$.

The skilled person will recognise that the 2D material can be selected to provide the desired properties of the Pickering emulsion, or of any solid produced from the Pickering emulsion. For example, graphene may be selected to provide electrical conductivity to the Pickering emulsion or a solid formed from the Pickering emulsion. Alternatively, hexagonal boron nitride may be selected to provide thermal conductivity to the Pickering emulsion or a solid formed from the Pickering emulsion. Other 2D materials such as molybdenum disulphide and tungsten disulphide are semiconductors.

The 2D material is an unfunctionalised or pristine 2D material. By unfunctionalised or pristine it is meant that the 2D material has not undergone any surface modification in order to change its surface tension. The term "unfunctionalised 2D material" therefore excludes, for example, graphene oxide.

Preferably, the 2D material is graphene, hexagonal boron nitride (h-BN), phosphorene or a transition metal dichalcogenide (TMD), more preferably graphene, hexagonal boron nitride or molybdenum disulphide. Most preferably, the 2D material is graphene.

As would be understood by the skilled person, in order to form a Pickering emulsion, the 2D material should have a surface tension which lies between that of the first and second liquid phases.

The surface tension of 2D materials can be estimated using known techniques, such as known from Hernandez et al., Langmuir, 2010, 26 (5), 3208-3213 and Hernandez et al., Nat. Nanotechnol, 2008, 3(9), 563-568. This technique is based on the maximum achievable concentrations of the material in dispersion. The surface tensions of various 2D materials are known in the art. For example, the surface tension of graphene is estimated to be in the range of about 41 to about 43 mN/m. The surface tensions of most 2D materials are similar. Preferably, the surface tension of the 2D material ranges from about 40 to about 50 mN/m.

The amount of 2D material that should be present in the Pickering emulsion of the invention may depend on the size of the droplets of the dispersed phase within the emulsion, the total volume of the dispersed phase, the nature of the 2D material and/or the nature of the liquid phases.

The particles of the 2D material are generally present in the Pickering emulsion in an amount sufficient to form a monolayer of particles around each of the droplets of the dispersed phase. Thus, in general, for a given volume of dispersed phase, a larger amount of 2D material will be required the smaller the size of the droplets of the dispersed phase.

In contrast to the method disclosed in US 2015/0348669, which simply blends together a mixture of liquids and graphite (i.e. a layered 3D material), the method of the present invention firstly exfoliates a layered 3D material to form a 2D material and secondly forms a Pickering emulsion stabilised by said 2D material. By exfoliating the layered 3D material before forming the emulsion it is possible to ensure that the 3D material is well exfoliated (i.e. that the 2D material formed consists of particles of 2D material no more than a few layers thick) before an emulsion is formed. Since the particles of 2D material are no more than a few layers thick, it is possible to form a monolayer of particles of 2D material around each of the droplets of the dispersed phase in the emulsion using less 2D material than would be required when each of the particles of 2D material comprises more layers of 2D material.

In this context, a few layers means 1 to about 10, preferably 1 to about 5, and more preferably 1 layer of atoms or formula units. Thus, it is preferred that the particles of 2D material are 1 to about 10, preferably 1 to about 5, and more preferably 1 layer of atoms or formula units thick.

The 2D material is generally present in the Pickering emulsion in the amount of less than about 5 vol. %, more preferably less than about 1 vol. %, most preferably less than about 0.1 vol. %, based on the volume of the dispersed phase. Generally, the 2D material is present in the Pickering emulsion in an amount of at least about 0.0001 vol. % based on the volume of the dispersed phase, such as from about 0.001 to about 5 vol. %, preferably from about 0.005 to about 1 vol. %, most preferably from about 0.01 to about 0.1 vol. %.

The vol. % of 2D material may be calculated by measuring the mass (as measured by weighing or by extinction spectroscopy) of 2D material present prior to formation of the emulsion. This is divided by the density of the bulk 3D material to give the volume of 2D material. This is then dived by the volume of the dispersed phase and expressed as a percentage by multiplying by 100. For example, 0.225 mg of graphene may be formed in 1 mL of cyclohexanone, after which 1 mL of water is added and a Pickering emulsion formed, wherein water forms the dispersed phase. In this example the volume of graphene is 0.000225 g/2.25 g/mL=0.0001 mL (the density of graphite is 2.25 g/mL). The vol. % of graphene based on the volume of dispersed phase (in this case water) is (0.0001/1)*100=0.01 vol. %.

Alternatively, the amount of 2D material may be expressed as a weight percent, calculated as the weight of 2D material divided by the weight of the dispersed phase (which can be calculated using the volume and density of the dispersed phase). In this case, the 2D material is generally present in the Pickering emulsion in the amount of less than about 10 wt. %, more preferably less than about 2 wt. %, more preferably less than about 1 wt. %, most preferably less than about 0.2 wt. %, based on the weight of the dispersed phase. Generally, the 2D material is present in the Pickering emulsion in an amount of at least about 0.0002 wt. % based on the weight of the dispersed phase, such as from about 0.002 to about 10 wt. %, preferably from about 0.01 to about 1 wt. %, most preferably from about 0.02 to about 0.2 wt. %.

Typically, the 2D materials used in the invention form layers which are one atom or formula unit thick. These layers are typically about 1 to about 5 nm thick. The 2D material used in the present invention is therefore in the form of particles or flakes which generally have a thickness of from about 1 to about 50 nm, more preferably about 1 to about 10 nm, most preferably about 1 to about 5 nm. As used herein, the term "particles" includes flakes. The particles generally have an aspect ratio (length to thickness) of greater than about 50. Thus, the particles of 2D material may have a (number) average length of about 50 nm to about 2000 nm, preferably from about 100 nm to about 1000 nm, more preferably from about 200 to about 500 nm, where the length is equivalent to the longest dimension of the flake or particle in the direction of the layer.

The particles may have an approximately round or square shape when viewed perpendicular to the 2D plane. Thus, the width of the particles may be approximately the same as the length. Alternatively, the particles of 2D material may have an approximately rectangular shape when viewed perpendicular to the 2D plane. Thus, the particles may have a (number) average width of about 20 nm to about 1000 nm, preferably from about 50 nm to about 700 nm, more preferably from about 100 to about 300 nm, where the width is equivalent to the longest dimension of the particle which is perpendicular to the length and in the direction of the layer. The aspect ratio (length to width) of the particles is preferably less than about 3.

The 2D materials may therefore be considered to be "nanomaterials". The size (e.g. length and width) and thickness of the particles of 2D material can be measured using atomic force microscopy, transmission electron microscopy or dynamic light scattering techniques.

The particles must be small enough that they can effectively coat the droplets of the dispersed phase in the emulsion. The smaller the particles of the 2D material are, the smaller the droplets can be while still being coated by the particles.

Liquid Phases

As discussed above, in order to form a Pickering emulsion the skilled person would understand that one of the liquid phases must have a surface tension which is higher than the surface tension of the 2D material, and the other liquid phase must have a surface tension which is lower than the surface tension of the 2D material. The first and second liquid phases must also be immiscible.

FIG. 9 is a table indicating whether a range of liquid phases are immiscible or miscible with each other. In FIG.

9, "0" indicates combinations which are miscible, and "1" indicates combinations which are immiscible. Whether other combinations of liquids are miscible or immiscible can be readily determined by simple mixing experiments.

Conveniently, graphene and similar 2D materials are known to have surface tensions between that of water and many water-immiscible liquids. This avoids the need to surface modify or functionalise the 2D material to adjust the surface tension of the 2D material such that a Pickering emulsion can be formed. Rather, a Pickering emulsion can naturally form using an un functionalised 2D material and two immiscible liquids such as water and a water-immiscible liquid. In contrast, clays and other silicates require surface modification to adjust the surface tension such that a Pickering emulsion can be formed. Such modifications are well known to compromise the properties of 2D materials. It is therefore highly advantageous to be able to avoid surface modification of the 2D materials used in the invention.

The surface tensions of most liquids are well known in the art, (see, for example, *Thermophysical Properties of Chemicals and Hydrocarbons*, Carl L. Yaw, William Andrew, Norwich, NY, 2008). Alternatively, the surface tension of a liquid can be readily characterised experimentally using the Wilhelmy plate method (as described, for example, in "Understanding Solvent Spreading for Langmuir Deposition of Nanomaterial Films: A Hansen Solubility Parameter Approach", Large et. al., Langmuir, A C S, 2017, DOI: 10.1021/acs.langmuir.7b03867). Such a method can be carried out using a Nima PS4 surface pressure sensor at 25° C. The surface tensions of some common liquids are shown in Table 1 below. All surface tensions referred to herein are the surface tensions as measured at 25° C.

TABLE 1

| Liquid | Surface tension ($\gamma$) (mN/m) |
| --- | --- |
| Pentane | 15.5 |
| Hexane | 17.9 |
| Acetone | 23.0 |
| Ethyl acetate | 23.2 |
| Methyl methacrylate | 24.2 |
| Cyclohexane | 24.7 |
| Butyl acrylate | 25.6 |
| Chloroform | 26.7 |
| Acrylonitrile | 26.7 |
| Dichloromethane | 27.8 |
| Styrene | 32.0 |
| Cyclopentanone | 33.4 |
| Cyclohexanone | 34.4 |
| N-cyclohexyl-2-pyrrolidone | 38.8 |
| Propylene glycol | 45.6 |
| Ethylene glycol | 48.4 |
| Diethylene glycol | 55.1 |
| Formamide | 57.0 |
| Water | 72.7 |
| Glycerol | 76.2 |

It is the relative rather than the absolute values of the surface tensions of the 2D material and the liquid phases which are important for emulsion formation. In particular, the Pickering emulsion is formed most readily when the magnitude of the difference between the surface tension of the first liquid phase and the surface tension of the 2D material is similar to the magnitude of the difference between the surface tension of the second liquid phase and the surface tension of the 2D material.

Thus, preferably the magnitude of the difference between the surface tension of the first liquid phase and the surface tension of the 2D material is within about 30 mN/m, more preferably within about 15 mN/m, more preferably within about 10 mN/m and most preferably within about 5 mN/m of the magnitude of the difference between the surface tension of the second liquid phase and the surface tension of the 2D material.

For example, one of the first and second liquid phases may have a surface tension which is from about 5 to about 35 mN/m higher than the surface tension of the 2D material, whilst the other liquid phase has a surface tension which is from about 5 to about 35 mN/m lower than the surface tension of the 2D material.

Alternatively, one of the first and second liquid phases may have a surface tension which is from about 10 to about 35 mN/m higher than the surface tension of the 2D material, whilst the other liquid phase has a surface tension which is from about 10 to about 35 mN/m lower than the surface tension of the 2D material.

Alternatively, one of the first and second liquid phases may have a surface tension which is from about 20 to about 35 mN/m higher than the surface tension of the 2D material, whilst the other liquid phase has a surface tension which is from about 20 to about 35 mN/m lower than the surface tension of the 2D material.

If the absolute values are considered, it is preferred that one of the first and second liquid phases has a surface tension of at least about 45 mN/m, more preferably at least about 50 mN/m, and most preferably at least about 60 mN/m, whilst the other liquid phase has a surface tension of less than about 45 mN/m, more preferably less than about 40 mN/m, and most preferably less than about 30 mN/m.

The choice of each liquid phase may depend on the intended use of the Pickering emulsion. For example, water is environmentally friendly. Ethyl acetate has a sufficiently low boiling point for use in preparing inks and is more environmentally friendly than some other organic liquids. Dichloromethane solubilises polydimethylsiloxane and so is suitable for formation of rubber composites.

One of the liquid phases is preferably selected from glycerol, water, formamide, diethylene glycol, ethylene glycol, propylene glycol or combinations thereof. More preferably, one of the liquid phases is selected from water, ethylene glycol, or combinations thereof. Most preferably, one of the liquid phases is water. Water is preferred not least for environmental reasons.

The other liquid phase is preferably selected from mineral oil, butadiene, methacrylic acid, acrylic acid, butyl acrylate, acrylonitrile, pentane, hexane, ethyl acetate, cyclohexane, chloroform, dichloromethane, methyl methacrylate, styrene, cyclopentanone, or combinations thereof. More preferably, the other liquid phase is selected from pentane, hexane, ethyl acetate, cyclohexane, chloroform, dichloromethane, methyl methacrylate, styrene, cyclopentanone, or combinations thereof.

Preferably, the first liquid phase is the liquid phase having a surface tension lower than that of the 2D material, and the second liquid phase is the liquid phase having a surface tension higher than that of the 2D material.

Each liquid phase may comprise a single liquid having the required surface tension, or may comprise a mixture of liquids provided that the mixture has the required surface tension relative to the other liquid phase and the 2D material. For example, mixtures of liquids may be used to control the surface tension, or to tune properties (e.g. the viscosity) of the emulsion. A mixture of water and ethylene glycol, for example, will have a surface tension between that of pure water and pure ethylene glycol.

Whilst other components may optionally be present in either or both of the liquid phases, the 2D material acts as a stabiliser for the Pickering emulsion. As a result, unlike traditional emulsions, no surfactant stabiliser is required. Preferably therefore, no surfactants are present in the Pickering emulsions of the present invention or the Pickering emulsions formed by the method of the invention.

One or both of the liquid phases may comprise further components, which may provide functionality to the Pickering emulsion. For example, at least one of the liquid phases may comprise or consist of monomers, and optionally also polymerisation initiators, to allow for polymerisation of the Pickering emulsion to form a polymeric solid.

Alternatively, at least one of the liquid phases may comprise active agents, for example pharmaceutically active compounds. In this case, the Pickering emulsion of the present invention could be used as a drug delivery system. For example, a pharmaceutical active present in the dispersed phase could be released by changing the surface tension of the continuous phase to invert the emulsion. The surface tension of the continuous phase could be changed using any suitable technique known in the art, for example by changing the concentration of solutes, for example sugars in an aqueous phase, or adding another liquid with a different surface tension.

Without wishing to be bound by theory, the Applicant believes that which one of the liquid phases forms the continuous phase and which liquid phase forms the dispersed phase is dependent on the spreading coefficients (S) of the liquids on the surface of the 2D material. Specifically, the liquid phase with the more negative spreading coefficient (corresponding to a higher affinity for the 2D material) will form the continuous phase and the liquid phase with the greater (less negative) spreading coefficient will form the dispersed phase. A rough approximation for the spreading coefficients for two liquids a and b can be determined as follows:

$$S_a = \gamma_{a,s} - \gamma_{b,s} - \gamma_{a,b}$$

$$S_b = \gamma_{b,s} - \gamma_{a,s} - \gamma_{a,b}$$

where $\gamma_{a,s}$ and $\gamma_{b,s}$ are the interfacial tensions between the 2D material and the liquids a and b respectively, and where $\gamma_{a,b}$ is the interfacial tension between the liquids a and b. The interfacial tensions between the liquids or between the 2D material and the liquids can be calculated using the following interfacial tension approximations:

$$\gamma_{a,b} = \gamma_a + \gamma_b - [4\gamma_a\gamma_b/(\gamma_a+\gamma_b)]$$

$$\gamma_{a,s} = \gamma_a + \gamma_s - [4\gamma_a\gamma_s/(\gamma_a+\gamma_s)]$$

$$\gamma_{b,s} = \gamma_b + \gamma_s - [4\gamma_b\gamma_s/(\gamma_b+\gamma_s)]$$

where $\gamma_a$, $\gamma_b$ and $\gamma_s$ are the surface tensions of the respective phases.

The orientation of the Pickering emulsions (i.e. oil-in-water or water-in-oil) may be more accurately described using surface energies of the three phases in place of the surface tensions. For liquids, the surface energy is equal to the sum of the surface tension and the surface entropy, where the surface entropy is 29 mJ/m² for all liquids at room temperature. Thus, for liquids the surface energy scales linearly with, and is therefore easily calculable from, the surface tension. For the 2D material, the surface energy can be measured. For example, the surface energy of each of graphene, hexagonal boron nitride and 2D molybdenum disulphide has been found to be around 70 mJ/m².

Emulsions

The (number) average (mean) diameter of the droplets within the Pickering emulsion which is formed is preferably about 150 μm or less, more preferably about 50 μm or less, and most preferably about 10 μm or less. Generally, the droplets have a (number) average diameter of at least about 100 nm, more preferably at least about 200 nm. For droplets above about 10 μm, optical microscopy can be used to measure the average diameters. Below this size, dynamic light scattering (DLS) can be used to measure the average diameters.

The Pickering emulsions of the invention or formed by the method of the present invention generally comprises at least about 97 vol. % liquid, preferably at least about 98 vol. % liquid, more preferably at least about 99.9 vol. % liquid, where the liquid includes both the continuous and dispersed phases.

Preferably, the Pickering emulsion comprises from about 50 to about 75 vol. % of the continuous liquid phase, based on the total volume of the liquid phases, and from about 25 to about 50 vol. % of the dispersed liquid phase, based on the total volume of the liquid phases.

Preferably, the liquid phase which forms the continuous phase and the liquid phase which forms the dispersed phase are present in a volume ratio of from about 3:1 to about 1:1 (continuous liquid phase to dispersed liquid phase), most preferably from about 2.5:1 to about 1.5:1, most preferably about 2:1.

The viscosity of the Pickering emulsion of the present invention will depend on the size of the droplets of the dispersed phase, the volume percentage of the dispersed phase, and the viscosity of the continuous phase. Thus, by controlling variables such as the volume percentage of dispersed liquid phase, it is possible to tailor the viscosity of the Pickering emulsion to the intended use.

Process of Making the Emulsion

The process of the invention comprises:
(a) exfoliating a layered 3D material in a solvent to produce particles of a 2D material;
(b) forming a dispersion of the particles of the 2D material in a first liquid phase;
(c) adding a second liquid phase and homogenising the dispersion of the 2D material in the first liquid phase with the second liquid phase to form a Pickering emulsion comprising the first liquid phase, the second liquid phase, and the particles of the 2D material.

In order to form a Pickering emulsion, one of the liquid phases should have a surface tension which is higher than the surface tension of the 2D material, and the other liquid phase should have a surface tension which is lower than the surface tension of the 2D material. In addition, the first and second liquid phases should be immiscible.

The first and second liquid phases, and the 2D material used in the method of the invention may comprise the liquids and materials discussed above.

Step (a)

Suitable methods for exfoliating layered 3D materials in a solvent to form particles of 2D materials are known in the art. For example, methods for exfoliating a layered 3D material to produce particles of a 2D material may comprise applying energy, e.g. ultrasound, to a layered 3D material in a solvent. Alternatively, shear force can be applied to a layered 3D material in a solvent. Suitable methods are disclosed in WO 2012/028724, WO 2014/001519 and US 2016/0009561.

Step (b)

In some embodiments, the solvent used in step (a) corresponds to the first liquid phase, and therefore step (b) is simply the result of carrying out step (a). In this case the solvent must be immiscible with the second liquid phase. However, in order to allow for better exfoliation of the 2D material, it is preferred that the solvent used in step (a) is different to the first liquid phase.

When the solvent used in step (a) is different to the first liquid phase, step (b) further comprises removing at least some of the solvent before adding a first liquid phase to form the dispersion of the 2D material in a first liquid phase. Thus, in this case step (b) comprises:
  (b1) removing at least some of the solvent and then adding a first liquid phase to form a dispersion of the particles of the 2D material in the first liquid phase.

Preferably, the majority of the solvent (at least about 50 wt. %) is removed in step (b1). More preferably, at least about 80 wt. %, and most preferably at least about 95 wt. % (such as about 100 wt. %) of the solvent is removed. Alternatively, all of the solvent may be removed.

The solvent may be removed by any suitable process. For example the dispersion may be centrifuged (e.g. at 5000 g for 24 hours) to sediment the 2D material, after which the supernatant (i.e. the solvent) can be discarded and the 2D material transferred into the first liquid phase. Alternatively, vacuum filtration can be used to prepare a "wet cake" of the exfoliated material which can be re-dispersed into an alternative solvent.

In the case where the solvent used in step (a) is different to the first liquid phase, it is preferred that the solvent used in step (a) is miscible with the first liquid phase in order to prevent formation of any unwanted emulsion during transfer of the particles to the first liquid phase. More preferably, the solvent is miscible with both the first liquid phase and the second liquid phase, in order to minimise any deviations in relative surface tensions of the two phases due to the presence of any residual solvent.

The solvent used in step (a) will depend in part on the material being exfoliated. As discussed above, methods for exfoliating 3D materials to form 2D materials are known in the art, for example from WO 2012/028724, WO 2014/001519, US 2016/0009561 and Hernandez et al., Langmuir, 2010, 26 (5), 3208-3213. The skilled person would therefore be able to select a suitable solvent for the 2D material being exfoliated.

For example, the solvent may be selected from N-methyl-2-pyrrolidone (NMP), N-cyclohexyl-2-pyrrolidone (CHP), 1,3-dimethyl-2-imidazolidinone (DMEU), N-ethyl-2-pyrrolidone (NEP), isopropanol, acetone, cyclopentanone (CPO) and cyclohexanone (CHO).

Preferably, the solvent used in step (a) has a surface tension of about 30 to about 50 mN/m. More preferably, the solvent used in step (a) has a surface tension which is approximately the same as that of the 2D material. Therefore, the solvent used in step (a) preferably has a surface tension of about 40 to about 50 mN/m, more preferably about 40 to about 45 mN/m.

Thus, preferably the solvent is selected from N-methyl-2-pyrrolidone (NMP), N-cyclohexyl-2-pyrrolidone (CHP), cyclopentanone (CPO) and cyclohexanone (CHO), more preferably cyclopentanone (CPO) and cyclohexanone (CHO). Cyclopentanone is particular preferred, especially for the exfoliation of graphene.

If the solvent used in step (a) is equivalent to the first liquid phase, it is preferred that the solvent is selected from cyclopentanone, cyclohexanone, and combinations thereof. In this case, the second liquid phase preferably comprises water.

Alternatively, the solvent used in step (a) may comprise a mixture of water and a surfactant. Any suitable surfactant may be used, such as an ionic or a non-ionic surfactant. The surfactant is ideally water-soluble. Triton X-100 is one example of a suitable non-ionic surfactant, and sodium cholate is one example of a suitable ionic surfactant.

The surfactant may be present in the solvent used in step (a) in the amount of from about 0.01 to about 0.05 wt. %, preferably from about 0.02 to about 0.03 wt %, based on the weight of water.

If the solvent in step (a) comprises water and a surfactant, it is necessary to remove at least part of the surfactant before forming the Pickering emulsion. As such, step (b) comprises step (b1), as described above. In this case, step (b1) comprises removing at least some of the mixture of water and surfactant, and then adding a first liquid phase, such as water (without any surfactant).

Step (c)

Step (c) comprises adding a second liquid to the dispersion of the 2D material in the first liquid phase, and then homogenising the two liquid phases and the 2D material to form a Pickering emulsion.

The homogenising step may simply comprise applying mechanical agitation to the mixture, such as by mixing or shaking the two liquid phases and the 2D material. Preferably, the mixture is homogenized by applying high shear forces, ultrasonic mixing, or by the use of a microfluidizer. A microfluidizer is preferred, as this allows for control of the droplet sizes and droplet size distribution in the resulting Pickering emulsion.

The viscosity of the resulting Pickering emulsion will depend on the droplet diameter, the volume percentage of the dispersed phase, and/or the viscosity of the continuous phase.

Figure 4:
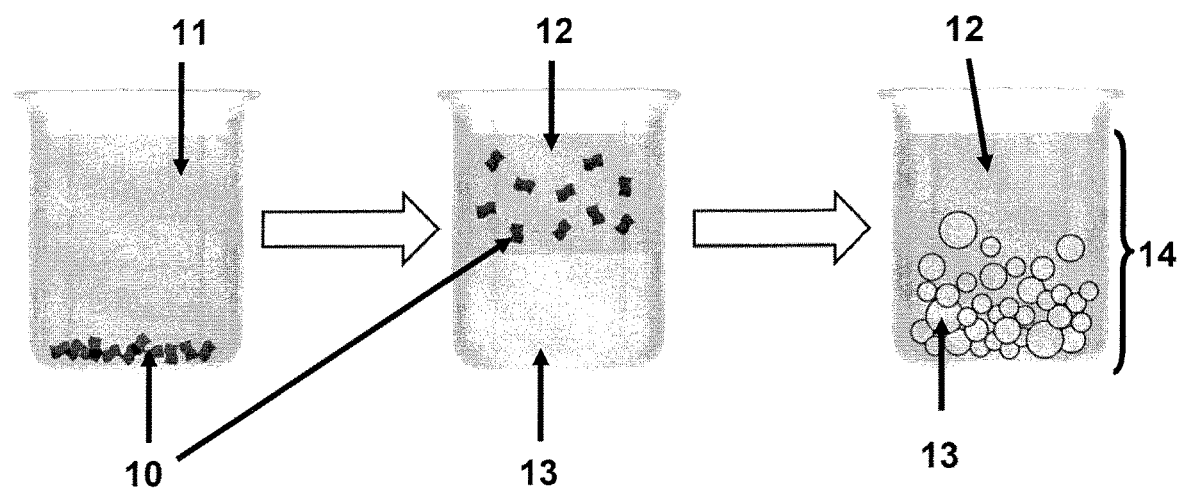
FIG. 4 is a schematic of a process of the invention.

The process discussed above is shown in schematic form in FIG. 4. FIG. 4 shows a process wherein a 2D material (10) is formed by exfoliating a layered 3D material in a solvent (11), after which the 2D material (10) is transferred (e.g. by a centrifugation process) to a first liquid phase (12), and a second liquid phase (13) is added. The liquid phases (12, 13) are then mixed and the emulsion is homogenised (e.g. through a high-shear mixing process such as ultrasonication or microfluidisation) to form the Pickering emulsion of the invention (14).

Uses

As discussed above, although methods for forming 2D materials are known in the art, the 2D material must generally be stabilised against re-aggregation. Such re-aggregation has been a long-standing roadblock to utilisation of 2D materials in macroscopic material systems at industrially relevant scales. The present inventors have found that Pickering emulsions comprising particles of 2D materials that were exfoliated from a 3D layered material before being formed into an emulsion are stable. Put another way, the Pickering emulsion stabilises the 2D particles against re-aggregation. Therefore, the Pickering emulsions of the present invention can be used to provide a highly stable form of the 2D material in particle form.

Solidification

In one aspect, the invention provides a solid structure formed from the Pickering emulsion of the invention. In such a solid structure the 2D material may impart useful properties to the solid. For example, conductive 2D materials such as graphene may allow for the formation of conductive solids. Solid structures formed from the Pickering emulsion of the present invention may therefore be suitable for a wide range of uses, as will be discussed further below.

Thus, the process of the invention may further comprise the step of forming a solid structure from the Pickering emulsion. This step may comprise freeze drying the Pickering emulsion, or polymerising monomers present in one or both of the liquid phases followed by drying the dispersion and thermal sintering or hot pressing to form a polymer composite suspension of solid particles, a porous foam, or a two-phase composite material.

If monomers forming all or part of both the droplet and/or continuous phase of the emulsion are polymerised, a polymer composite may be formed.

Where this step comprises polymerising monomers present in one or both of the liquid phases, a reaction initiator should also be present in the phase to be polymerised in order to drive the reaction. Suitable reaction initiators are known in the art. For example, radical initiators such as N,N-dimethylaniline and benzoyl peroxide may be used. Typically, the initiator is added to the monomer phase just prior to the homogenisation step (step (c)), and the reaction is allowed to proceed to completion.

For example, if monomers forming all or part of the continuous phase of the emulsion are polymerised, a porous foam-like material will be produced containing the particles of the 2D material. In this case, the dispersed phase may evaporate over time, with the rate of evaporation depending on how rapidly the dispersed phase can diffuse out of the composite system.

Alternatively, if monomers forming all or part of the droplet phase of the emulsion are polymerised, a suspension of solid polymer particles in the continuous phase may be formed. The polymerisation may also result in the formation of polymer coated particles of the 2D material. The continuous phase may then be evaporated to produce a powder that may be processed into a solid composite or porous sintered foam.

The monomers preferably form one of the first and second liquid phases. For example, styrene, a mixture of styrene and butadiene, methyl methacrylate, methacrylic acid, acrylic acid, butyl acrylate, or a mixture of acrylonitrile and butadiene can be used as one of the liquid phases in the emulsion.

Figure 5:
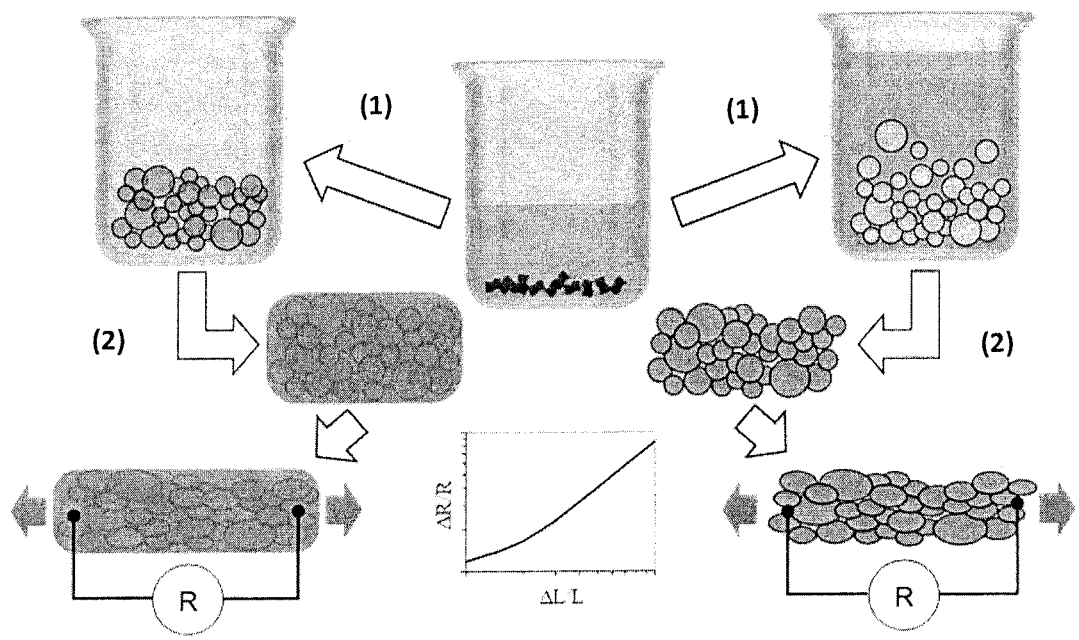
FIG. 5 is a schematic of a process of the invention and forming a solid structure from said emulsion.

FIG. 5 shows two approaches to forming functional elastomer composites for sensing. A 2D material (e.g. graphene) is used to stabilise an emulsion comprising two liquid phases, where at least one phase comprises a monomer (e.g. styrene-butadiene). Step (1) comprises ultrasonication/high-shear mixing. Depending on the liquids and 2D material selected, the liquid comprising the monomer may form the continuous phase (left route) or discontinuous phase (right route). The liquid phase comprising the monomer is subsequently polymerised and dried (step (2)). A porous foam (left route) or composite of packed spheres (right route) is formed which exhibits a resistive response to applied strain.

Solids

In recent years, fossil fuel based energy sources have started to be replaced with renewable energy sources. One issue with renewable energy is inherent supply variability. Grid level energy storage allows the supply variation to be smoothed, and is therefore integral to the widespread adoption of renewable energy generation as a fossil fuel replacement. Improvements to the energy density, current capacity and fabrication techniques of electrical energy storage would prove invaluable to grid-based energy storage systems. Better energy storage solutions would also greatly assist the development of electric vehicles.

The properties and high specific surface area of many 2D materials makes them ideal for forming supercapacitors and electrochemical battery devices. In addition, solid devices formed using the emulsions of the present invention should have a high power density due to the good mobility of ions through the porous structure.

As discussed above, the emulsions of the present invention may be formed into solid structures by, for example, polymerising one or both of the liquid phases within the emulsion. The solids formed may be used in electrochemical applications, for example in supercapacitors, batteries, electrocatalysis and photocatalysis.

For example, emulsions comprising graphene as the 2D material could be used to form electrodes by thermal sintering. Similarly, an emulsion wherein the 2D material is hexagonal boron nitride could be used to produce a porous, insulating spacer layer, whilst emulsions containing molybdenum disulphide could be used to form a hydrogen evolution catalyst or a battery electrode for sodium ion cells.

Emulsion polymerised elastomer composites with functional properties prepared from the Pickering emulsions of the invention have utility in wearable sensor applications in sport science and physiotherapy, as well as smart textiles and wearable technology. These applications require high strain sensitivity and frequency response to monitor joint extension on the human body. Sensing elements could be prepared by polymerising either the continuous phase of the Pickering emulsion of the invention (to produce foam-like structures) or the discontinuous phase and casting continuous films.

Other uses for solid structures formed from the Pickering emulsions of the present invention may include mechanical reinforcement of 2D material polymer composites, electrical percolation in 2D material polymer composites, graphene elastomer composite strain sensors, scaffolds for tissue culture, and 2D material polymer composite foams for water purification.

Liquid Strain Gauge

A Pickering emulsion stabilised by a non-silicate 2D material may be used to form a liquid strain gauge if a conductive non-silicate 2D material, preferably graphene, is used as the 2D material.

Thus, in one aspect, the invention provides a liquid strain sensor comprising a Pickering emulsion stabilised by a non-silicate 2D material, such as a Pickering emulsion formed using the method of the present invention, wherein the 2D material is electrically conductive. For example, the liquid strain sensor may comprise a closed pipe or channel containing a Pickering emulsion stabilised by a 2D material, wherein the 2D material is electrically conductive. Preferably, the pipe is a silicone pipe.

The Pickering emulsions formed using the method of the present invention can be considered to have an effective surface conductivity due to the near-continuous coverage of the dispersed phase droplets with the stabilising conductive particles. As the droplets are deformed under strain transfer from the pipe or channel, their surface area-to-volume ratio increases. Increases in the inter-particle separation on the droplet surfaces lead to rapid and reversible rise in the resistance observed. As a result, the device shows a large resistance change with strain.

Liquid strain sensors comprising a Pickering emulsion stabilised by a non-silicate 2D material, such as a Pickering emulsion formed using the method of the present invention, can have extremely high gauge factors. For example, the gauge factor of the liquid strain sensor of the invention may be at least 30, more preferably at least 35, and most preferably at least about 40.

The sensitivity of the liquid strain gauge described herein is sufficiently high that they can be used to track the respiration rates and pulses of people wearing the device. For example, the liquid strain gauge could be incorporated into a 'fitness tracker'-like band, or even embedded within the fabric of an item of clothing such as a baby sleep suit. Such devices can provide a comfortable, non-invasive way to monitor the breathing and heart rate of a subject. This can be useful in any area where it is desirable to monitor respiration and heart rates, for example to monitor sleep apnea, heart and respiration rates during exercise, or the breathing and heart rate of babies.

Ink Compositions

A Pickering emulsion stabilised by a non-silicate 2D material may be used as an ink which can deposit the 2D material onto a substrate. The 2D material may provide functional properties to the ink composition, such as electrical or thermal conductivity.

Thus, in one aspect, the present invention provides the use of a Pickering emulsion stabilised by a non-silicate 2D material, such as a Pickering emulsion formed using the method of the present invention, as an ink. The ink may be an electrically or thermally conductive ink, or a semiconductive ink, if the 2D material is electrically or thermally conductive, or semiconductive. The ink may be used in any form of printing, such as inkjet printing or screen printing, or could be printed using other methods including doctor blading, spin coating or slot die coating.

In another aspect, the present invention provides a method of printing, comprising applying an ink comprising a Pickering emulsion stabilised by a non-silicate 2D material, such as a Pickering emulsion formed using the method of the present invention, to a substrate, and subsequently drying the substrate. This printing process may comprise any form of printing, such as inkjet printing or screen printing.

For example, when a conductive 2D material, preferably graphene, is used to stabilise a Pickering emulsion, the emulsion may be used as a conductive ink composition for use in printing, such as in inkjet printing or screen printing. Suitable substrates are known in the art and include paper and polymeric materials.

When a semiconducting 2D material, preferably a semiconducting transition metal dichalcogenide such as molybdenum disulphide, is used to stabilise a Pickering emulsion, the emulsion may be used as an ink composition for the deposition of transistors using known printing techniques.

Regardless of the nature of the 2D material, when using a Pickering emulsion stabilised by a non-silicate 2D material, including Pickering emulsions formed using the method of the present invention, as an ink, it is preferred to use a liquid phase having a low boiling point (such as about 120° C. or less, preferably about 110° C. or less, more preferably about 100° C. or less at atmospheric pressure) as the continuous phase in order to allow for easy and efficient drying of the ink when printed. Most preferably, when using Pickering emulsions as an ink it is preferred that the liquid comprising the continuous phase comprises water, ethyl acetate, or a combination thereof, since both of these liquids have relatively low boiling points and are relatively environmentally friendly compared to other possible liquid phases.

Conventional conductive ink compositions generally comprise a conductive material, an organic solvent, a stabiliser (e.g. a surfactant), a polymer binder, and/or a viscosity modifier (e.g. short-chain polyethylene glycol). The additional components such as stabilisers all affect the conductivity of the ink, since they remain on a substrate once the ink has dried.

Pickering emulsions stabilised by a non-silicate 2D material, such as Pickering emulsions formed using the method of the invention, are stable without the addition of stabilisers or viscosity modifiers. The viscosity of the emulsions can be controlled by varying the nature of the continuous phase and/or the volume percentage of the droplets within the emulsion and/or the size of the droplets within the emulsion. There is therefore no need to include additional components such as a binder or a viscosity modifier, which can negatively impact the properties (e.g. conductivity) of the ink once printed.

Thus, Pickering emulsions stabilised by a non-silicate 2D material can be used as inks which simply comprise a non-silicate 2D material, a first liquid phase and a second liquid phase. Once the liquids evaporate, the dried ink comprises just the 2D material, thereby ensuring good properties (e.g. conductivity) of the dried ink.

Furthermore, conventional conductive inks may comprise no more than about 2 wt. % of conductive material before a slurry forms, and/or the conductive material starts to aggregate. In contrast, when using Pickering emulsions stabilised by a non-silicate 2D material, such as the Pickering emulsions formed by the method of the present invention, the emulsions may comprise significantly higher amounts of 2D material.

Figure 10:
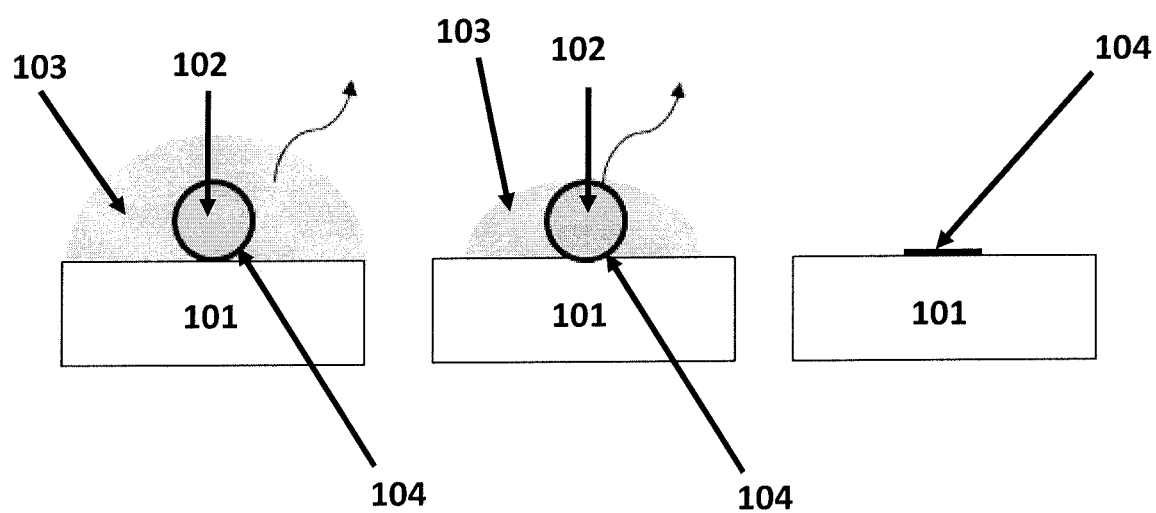
FIG. 10 shows a process of depositing an ink comprising a Pickering emulsion on a substrate.

For example, the emulsions may comprise up to about 10 wt. % of 2D material. In addition, inks formed from the Pickering emulsions described herein have the added advantage over inks formed from standard dispersions that the deposition process is more controlled. For example, when a Pickering emulsion which is a water-in-oil emulsion is deposited onto a hydrophobic (polymer) substrate (101), the water droplets (102) remain stable whilst the oil phase (103) spreads and evaporates. Once sufficient evaporation has occurred to expose the water droplets to air, the water droplets (which are coated in the 2D-material (104)) will collapse onto the substrate, because the water droplets are unstable at the interface between the air, the water, and the 2D-material. This results in a more controlled deposition and a reduced "coffee-ring" effect compared to other deposition processes. This process is illustrated schematically in FIG. 10.

When forming emulsions for use in inkjet printing, it is generally desired for the number average (mean) diameter of the droplets (i.e. the dispersed phase) within the emulsion to be about 10 μm or less. In order to achieve this droplet size it is generally necessary to use a microfluidizer when forming the emulsion. Thus, step (c) of the method set out above may comprise:

(c1) adding a second liquid phase and homogenising the dispersion of the 2D material in the first liquid phase with the second liquid phase with a microfluidizer to form a Pickering emulsion comprising the first liquid phase, the second liquid phase, and the 2D material, where the number average diameter of droplets of the dispersed phase within the emulsion is about 10 μm or less.

Inks of the present invention have been deposited by hand to form conductive films, which have been found to exhibit conductivities comparable to those of films of graphene and $MoS_2$ formed by other techniques.

PREFERRED EMBODIMENTS

It is understood that any and all features of the present invention may be taken in conjunction with any other feature or features to describe additional embodiments of the invention. Some particularly preferred embodiments are described below.

In one embodiment, one of the liquid phases is water.

In one embodiment, one liquid phase comprises or consists of water and the other liquid phase comprises or consists of cyclopentanone and/or cyclohexanone.

In one embodiment, one liquid phase comprises or consists of ethyl acetate and the other liquid phase comprises or consists of water, formamide, ethylene glycol or a combination thereof.

In one embodiment, one liquid phase comprises or consists of water, formamide, ethylene glycol or a combination thereof, and the other comprises or consists of methyl methacrylate, butyl acrylate and/or styrene.

In one embodiment, the particles of 2D material have a (number) average length of about 50 nm to about 2000 nm, a (number) average width of about 20 nm to about 1000 nm, and an aspect ratio of length to thickness of greater than about 50.

In one embodiment, the amount of 2D material present in the Pickering emulsion is from about 0.001 to about 5 vol. %, based on the volume of the dispersed phase, and the dispersed phase comprises droplets having an average diameter of about 50 μm or less.

In one embodiment, the amount of 2D material present in the Pickering emulsion is from about 0.01 to about 0.1 vol. %, based on the volume of the dispersed phase, and the dispersed phase comprises droplets having an average diameter of about 10 μm or less.

All documents referred to herein are incorporated by reference.

EXAMPLES

Materials

Graphite powder (supplied by Zenyatta Ventures Ltd) with a nominal 3.5 μm particle size was used as-received.

Hexagonal boron nitride powder (supplied by Thomas Swan Ltd) was prepared in surfactant solution according to the procedure set out in K. R. Paton et al. "Scalable Production of Large Quantities of Defect-Free Few-Layer Graphene by Shear Exfoliation in Liquids" (*Nature Materials* 13.6 (2014), pp. 624-630). This was subsequently dried and washed.

$MoS_2$, $MoSe_2$, and $WS_2$ powders were purchased from Sigma Aldrich. These sieved powders (with 1 to 2 μm particle sizes) were used as-received.

A commercially available brand of baby oil was purchased and used as-received; the primary constituent was paraffin oil.

Type 1 purified water (18.2 MΩ cm resistivity) was prepared using a Thermo Scientific MicroPure filtration system.

The surface tensions of the liquids used were characterised using the Wilhelmy plate method using a Nima PS4 surface pressure sensor at 25° C.

Example 1—Formation of Pickering Emulsions 0.4 g of graphite powder was ultrasonically exfoliated into 20 mL of baby oil. Sonication was performed using a Sonics Vibracell VCX750 probe sonicator with output pulsing (6 s on, 2 s off) and 60% tip amplitude (~45 W power) for 3 hours. The sonicated dispersion was further diluted with baby oil to achieve a volume fraction of graphene of 0.05 vol. %.

This was repeated with different levels of dilution to form samples containing volume fractions of graphene of 0.1 vol. %, 0.2 vol. %, 0.3 vol. %, 0.4 vol. %, 0.5 vol. % and 0.75 vol. %.

For each sample, a dispersion of multilayer graphene nanoparticles with a modal thickness of approximately 10 nm was formed, as measured by atomic force microscopy.

2 mL of water was added to 4 mL of each dispersion of graphene in baby oil, and each mixture was then homogenised, first by shaking and subsequently by ultrasonic mixing for 30 seconds, to form a Pickering emulsion.

Figure 6:
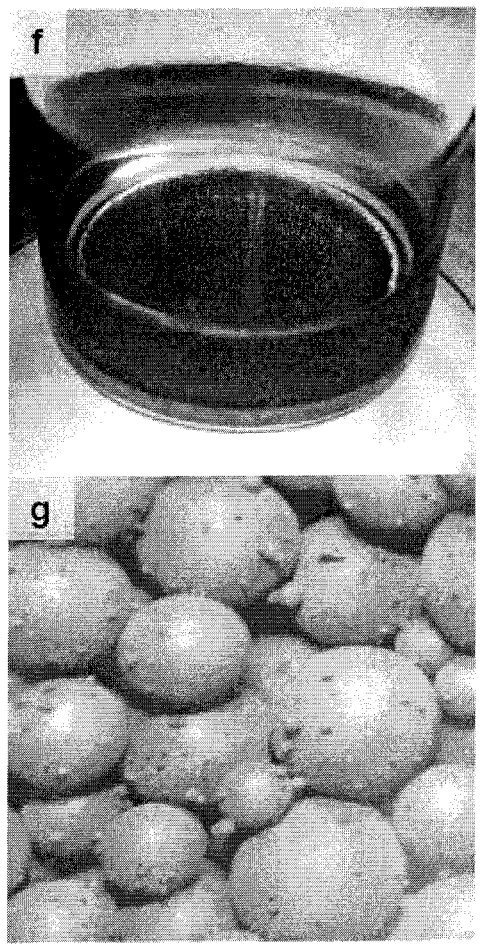
FIG. 6 shows a photograph and an optical micrograph of a Pickering emulsion formed using the method of the invention with graphene as the solid stabiliser.

FIG. 6 shows a photograph (f) and optical micrograph (g) of the Pickering emulsion containing 0.2 vol. % graphene, based on the volume of baby oil. The Pickering emulsion remained stable for several months in a sealed container at a temperature of approximately 22° C.

Example 2

The process of Example 1 was repeated using other 2D materials, which were produced by exfoliating hexagonal boron nitride, $MoS_2$, $MoSe_2$, and $WS_2$ powders in baby oil.

Figure 7:
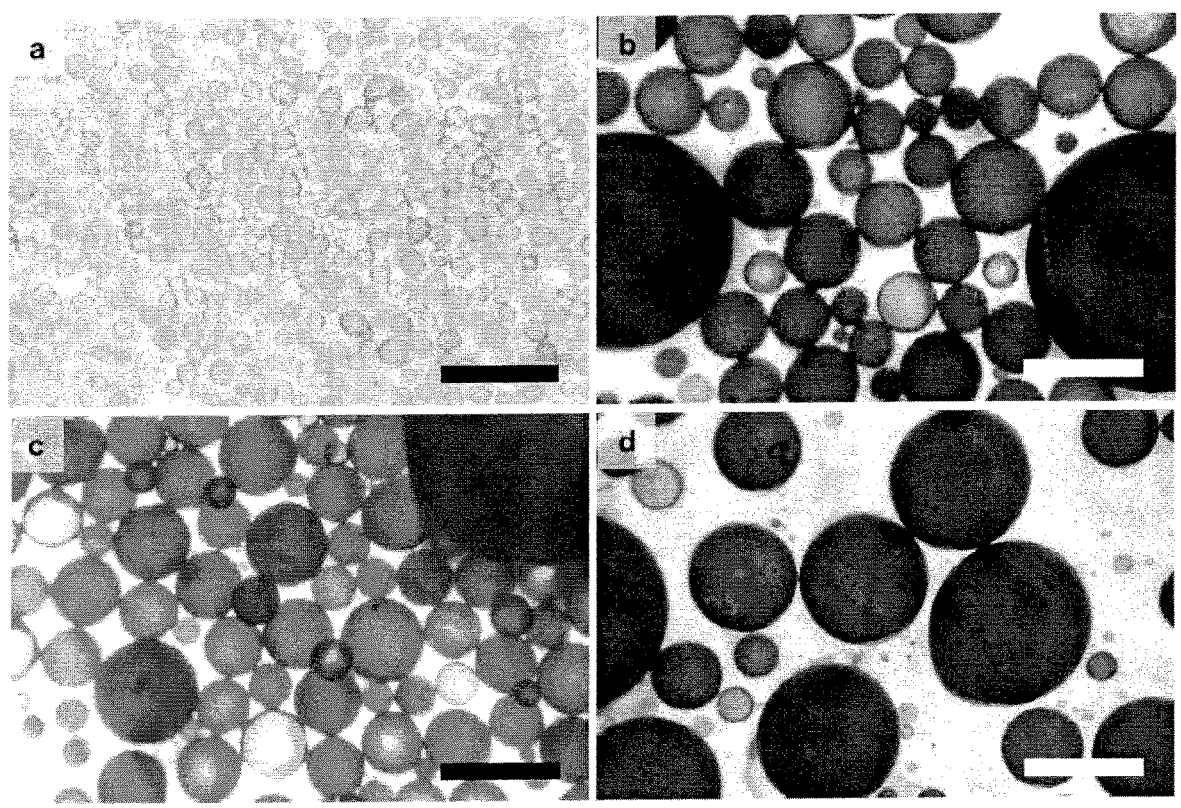
FIG. 7 shows optical micrographs of Pickering emulsions formed using the method of the invention stabilised with (a) boron nitride, (b) molybdenum disulphide, (c) tungsten disulphide, and (d) molybdenum diselenide.

FIG. 7 shows optical micrographs of Pickering emulsions wherein the 2D material is hexagonal boron nitride (a), molybdenum disulphide (b), tungsten disulphide (c) and molybdenum diselenide (d). The scale bars in FIG. 7 are 1 mm.

Example 3—Liquid Strain Gauge

The Pickering emulsion formed in Example 1 containing 0.2 vol. % graphene based on the volume of baby oil was encapsulated in a silicone pipe with electrical end contacts.

Figure 8:
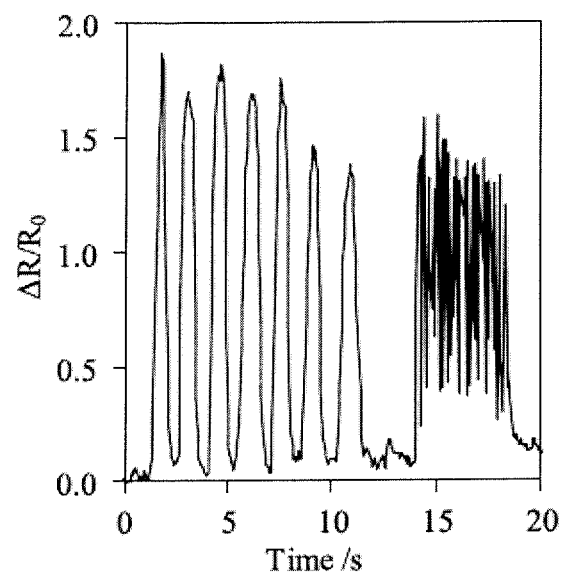
FIG. 8 is a plot of relative resistance change $\Delta R/R_0$ against time for a liquid strain sensor of the invention.

FIG. 8 is a plot of relative resistance change $\Delta R/R_0$ against time under repeated manual strain for the strain sensor. The first range shows a strain of approximately 5% with a frequency of 0.7 Hz, followed by a similar strain with a frequency of 5.3 Hz.

Based on the approximate amplitudes of the strain and resistance change measured, the gauge factor of the system shown was approximately 40. This is the highest reported for a liquid. Thus, the Pickering emulsions of the invention provide a liquid-based strain sensor which has a simple preparation procedure, with potential for integration into a range of applications.

Example 4—Formation of Solid Material

In order to prepare polymerised materials, an initiator system comprising benzoyl peroxide and N,N-dimethylaniline was used.

100 μg of 2D molybdenum disulphide was added to a liquid phase comprising 2 mL ethylene glycol.

Separately, 0.05 g of benzoyl peroxide was added to 1 mL of methyl methacrylate, and 0.02 mL of N,N-dimethylaniline was then added to the mixture.

The two liquid phases were promptly emulsified, with the ethylene glycol forming the continuous phase and the methyl methacrylate liquid phase forming the droplet phase. The droplet phase was then polymerised, and the polymerisation reaction was allowed to proceed to completion (5 hours at 25° C.).

Polymerised droplets coated with molybdenum disulphide were formed, and were allowed to sediment. The ethylene glycol was removed and replaced with water. The sample was subsequently dried to yield a powder that may be subsequently processed.

Example 5—Solvent Exchange

Graphite was added to 80 mL of cyclopentanone at a concentration of 50 mg/mL. This dispersion was ultrasonicated using a Sonics Vibracell VCX750 probe sonicator 60% tip amplitude (~45 W power) for 3 hours in an ice bath.

Un-exfoliated material was removed from the dispersion by performing centrifugation at 5000 g for 10 minutes in a Thermo Scientific Sorvall Legend X1 centrifuge. The supernatant was collected. In order to recover the exfoliated graphene and transfer it to the first liquid phase, this supernatant was centrifuged at 5000 g for 10 hours, and the supernatant (solvent) was discarded. 500 µg of sediment from the second centrifuge step (i.e. the exfoliated graphene) was dispersed in 5 mL of ethylene glycol (a first liquid phase) and formed into a Pickering emulsion with 10 mL of chloroform (a second liquid phase).

Example 6—Conductivity

Emulsions were prepared by ultrasonic exfoliation (~20 W) of graphite in 25 mL CHO and $MoS_2$ in 25 mL CPO for 3 hours to give emulsions containing 25 g/L of 2D material.

The samples were then centrifuged at 5000 g for 5 minutes to remove any unexfoliated 3D material. The resultant dispersions were then emulsified with deionized (DI) water to give Pickering emulsions containing droplets with a diameter of 10 to 100 microns. The average droplet sizes were measured by statistical optical microscopy.

Conductivity of the Pickering emulsion was determined by transferring the emulsion into a polytetrafluoroethylene trough with copper tape end contacts, and measuring electrical resistance before normalising to the sample geometry.

The measured conductivities showed a clear dependence on loading level/droplet size, with conductivity increasing with decreasing loading level/droplet size. The conductivity was found to be almost independent of the 2D-material, indicating that the network resistance was limited by inter-droplet "junctions" where the conductivity of the matrix phase (i.e. CHO or CPO) determines the absolute conductivities. The effect of these junctions can be reduced at higher loading levels/smaller droplet size.

The invention claimed is:

1. A method for making a Pickering emulsion, the method comprising:
   (a) exfoliating a non-silicate layered 3D material in a solvent to produce particles of a non-silicate unfunctionalized 2D material;
   (b) removing at least about 50 wt. % of the solvent and then adding a first liquid phase to form a dispersion of the particles of the 2D material in a first liquid phase;
   (c) adding a second liquid phase and homogenizing the dispersion of the 2D material in the first liquid phase with the second liquid phase to form a Pickering emulsion comprising the first liquid phase, the second liquid phase, and the particles of the 2D material.

2. The method of claim 1, wherein the unfunctionalized 2D material is graphene, borophene, germanene, silicene, stanene, phosphorene, bismuthene, hexagonal boron nitride, MXenes, 2D perovskites, or transition metal dichalcogenides.

3. The method of claim 1, wherein the solvent used in step (a) is different from the first liquid phase.

4. The method of claim 1, wherein the solvent is selected from N-methyl-2-pyrrolidone, N-cyclohexyl-2-pyrrolidone, 1,3-dimethyl-2-imidazolidinone, N-ethyl-pyrrolidone, isopropanol, acetone, cyclopentanone and cyclohexanone, or a mixture of water and a surfactant.

5. The method of claim 1, wherein the magnitude of the difference between the surface tension of the first liquid phase and the surface tension of the 2D material is within 30 mN/m of the magnitude of the difference between the surface tension of the second liquid phase and the surface tension of the 2D material.

6. The method of claim 1, wherein one of the first and second liquid phases has a surface tension which is from about 5 to about 35 mN/m higher than the surface tension of the 2D material, whilst the other liquid phase has a surface tension which is from about 5 to about 35 mN/m lower than the surface tension of the 2D material.

7. The method of claim 1, wherein the first liquid phase has a surface tension lower than that of the 2D material, and the second liquid phase has a surface tension higher than that of the 2D material.

8. The method of claim 1, wherein the first liquid phase is pentane, hexane, ethyl acetate, cyclohexane, chloroform, dichloromethane, methyl methacrylate, styrene, cyclopentanone, or combinations thereof.

9. The method of claim 1, wherein the second liquid phase is glycerol, water, formamide, diethylene glycol, ethylene glycol, propylene glycol, or combinations thereof.

10. The method of claim 1, wherein the particles of the 2D material are from 1 to 5 nm thick, and have an average length of from about 50 nm to about 2000 nm.

11. The method of claim 1, wherein the 2D material is graphene, hexagonal boron nitride, phosphorene or a transition metal dichalcogenide.

12. The method of claim 1, wherein the mixture is homogenized in step (c) by applying high shear forces, ultrasonic mixing, or by the use of a microfluidizer.

13. The method of claim 1, wherein step (c) comprises:
   (c) adding a second liquid phase and homogenizing the dispersion of the 2D material in the first liquid phase with the second liquid phase with a microfluidizer to form a Pickering emulsion comprising the first liquid phase, the second liquid phase, and the 2D material, where the average diameter of droplets of the dispersed phase within the emulsion is about 10 µm or less.

14. The method of claim 1, further comprising the step of forming a solid structure from the Pickering emulsion.

15. The method of claim 14, wherein one or both of the liquid phases comprises monomers and a reaction initiator, and wherein the step of forming a solid structure from the Pickering emulsion comprises polymerizing the monomers.

16. The method of claim 15, wherein the monomers comprise styrene, methyl methacrylate, methacrylic acid, acrylic acid, butyl acrylate, a mixture of styrene and butadiene, or a mixture of acrylonitrile and butadiene.

17. A method for making a Pickering emulsion, the method comprising:
   (a) exfoliating a non-silicate layered 3D material in a solvent to produce particles of a non-silicate unfunctionalized 2D material;
   (b) forming a dispersion of the particles of the 2D material in a first liquid phase;
   (c) adding a second liquid phase and homogenizing the dispersion of the 2D material in the first liquid phase with the second liquid phase to form a Pickering emulsion comprising the first liquid phase, the second liquid phase, and the particles of the 2D material;
wherein the solvent is selected from N-methyl-2-pyrrolidone, N-cyclohexyl-2-pyrrolidone, 1,3-dimethyl-2-imidazolidinone, N-ethyl-2-pyrrolidone, isopropanol, acetone, cyclopentanone and cyclohexanone.

18. The method of claim 17, wherein the solvent is selected from cyclopentanone and cyclohexanone.

19. A method for making a Pickering emulsion, the method comprising:
   (a) exfoliating a non-silicate layered 3D material in a solvent to produce particles of a non-silicate unfunctionalized 2D material;
   (b) removing at least about 50 wt. % of the solvent and then adding a first liquid phase to form a dispersion of the particles of the 2D material in a first liquid phase;
   (c) adding a second liquid phase and homogenizing the dispersion of the 2D material in the first liquid phase with the second liquid phase to form a Pickering emulsion comprising the first liquid phase, the second liquid phase, and the particles of the 2D material, and
   wherein the unfunctionalized 2D material is graphene, borophene, germanene, silicene, stanene, phosphorene, bismuthene, hexagonal boron nitride, MXenes, or 2D perovskites.

* * * * *